United States Patent [19]

Hull

[11] Patent Number: 4,933,543

[45] Date of Patent: Jun. 12, 1990

[54] DARK SIGNAL COMPENSATION FOR DIODE ARRAYS

[75] Inventor: Frank A. Hull, Circle Pines, Minn.

[73] Assignee: Chesley F. Carlson, Plymouth, Minn.

[21] Appl. No.: 101,359

[22] Filed: Sep. 25, 1987

[51] Int. Cl.$^5$ .............................................. H01J 40/14
[52] U.S. Cl. .................................. 250/214 C; 250/238
[58] Field of Search ............... 250/214 C, 238, 352, 250/214 R; 358/213.16, 221; 455/619

[56] References Cited

U.S. PATENT DOCUMENTS

| | | | |
|---|---|---|---|
| 3,877,817 | 4/1975 | Ralston | 250/238 |
| 4,438,348 | 3/1984 | Casper et al. | 250/214 C |
| 4,619,533 | 10/1986 | Lucas et al. | 250/352 |
| 4,678,914 | 7/1987 | Melrose et al. | 250/352 |
| 4,766,304 | 8/1988 | Kihara et al. | 250/214 C |

*Primary Examiner*—David C. Nelms
*Attorney, Agent, or Firm*—Dorsey & Whitney

[57] ABSTRACT

Three means or methods for compensating for thermal noise, also referred to as dark signal, are utilized to enhance the accuracy of a monolithic diode array. A charge-coupled linear photodiode array is used in a camera to detect densities of any image projected or reflected onto the array. After conversion, voltage variations of one/one thousandth (1/1,000) volt in a ten volt range are significant to the measurement of densities. Therefore, extremely accurate control of thermal noise, which is generated in the cell sites and in the shift registers used to obtain the data from the cell sites, is extremely important. The three methods or means of control are as follows. Temperature control maintains the temperature of the photodiode array at approximately ten degrees centigrade to minimize the generation of thermal noise. A thermistor is used to detect any temperature variations within the range controlled by the cooling means and the reading is compensated for those variations in temperature. Finally, thermal noise generated in masked cells are measured and used as a correction or calibration for the readings. The foregoing means and methods enhance the accuracy of the readings by an order of magnitude.

14 Claims, 9 Drawing Sheets

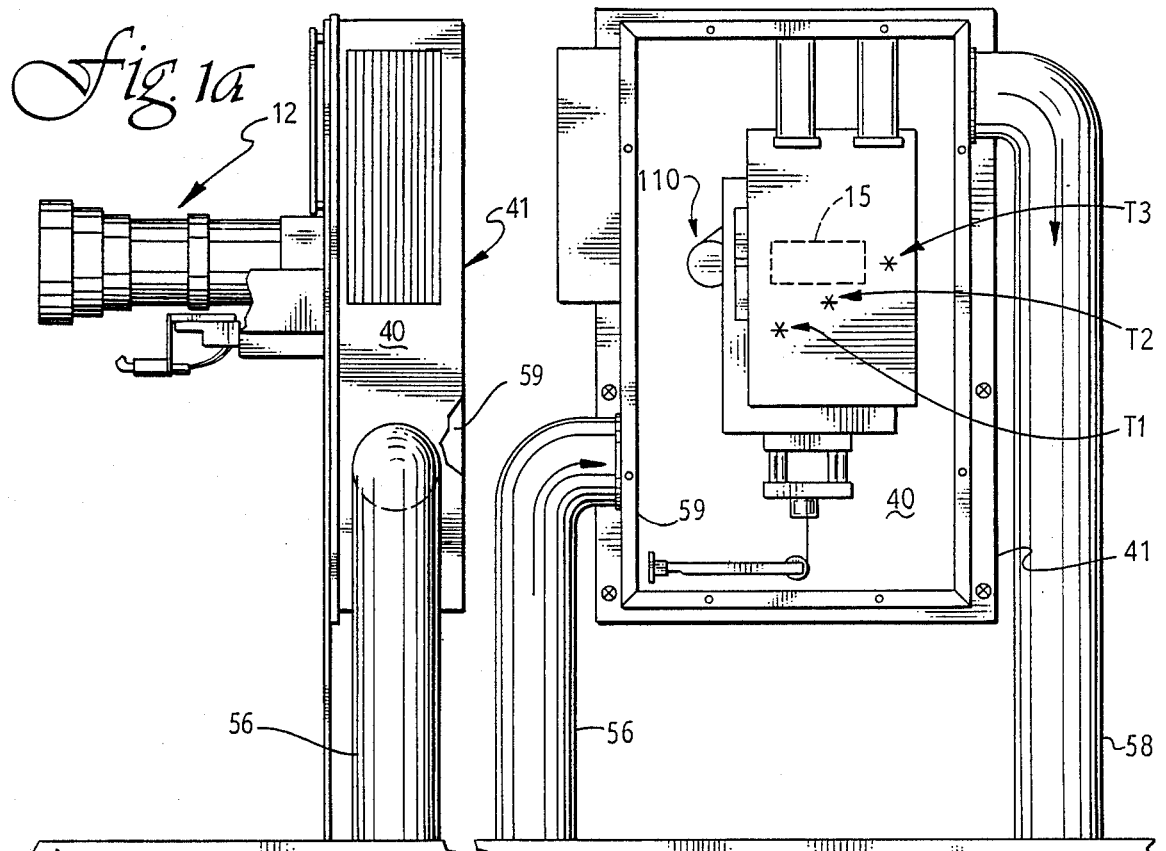
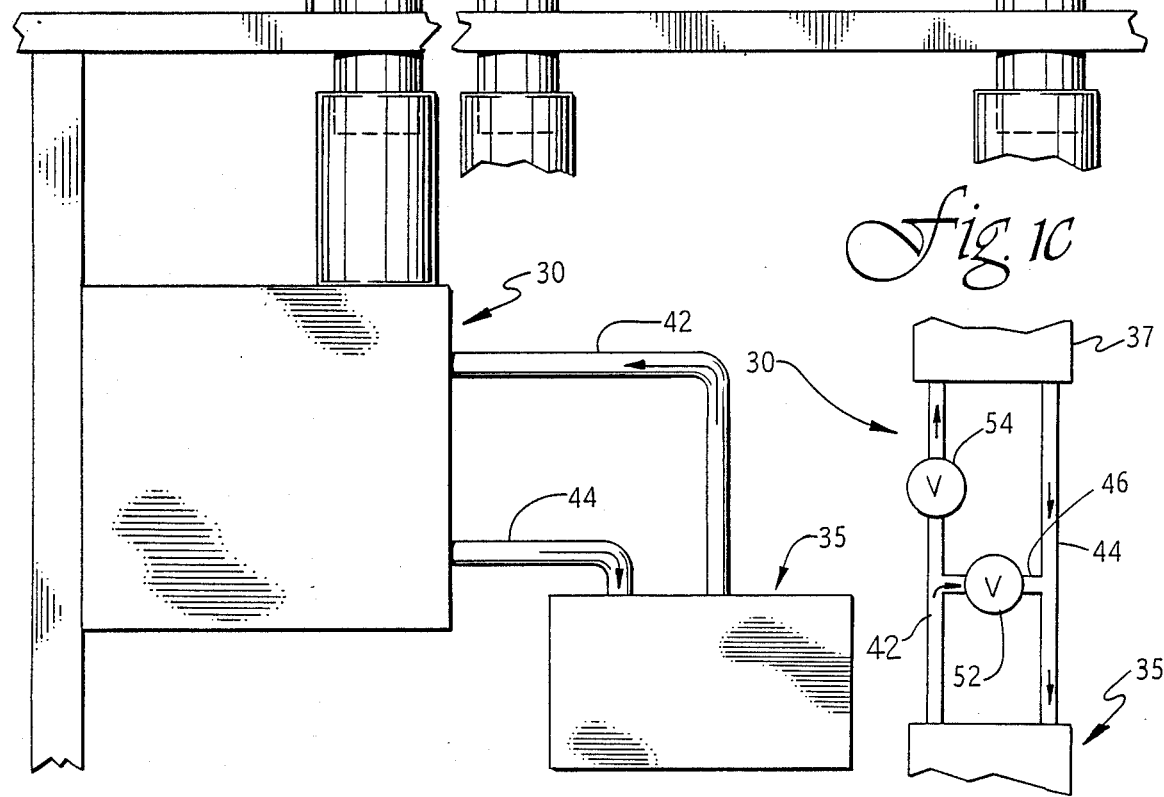

Fig. 2

| Fig. 2a | Fig. 2b |
|---------|---------|
| Fig. 2c | Fig. 2d |

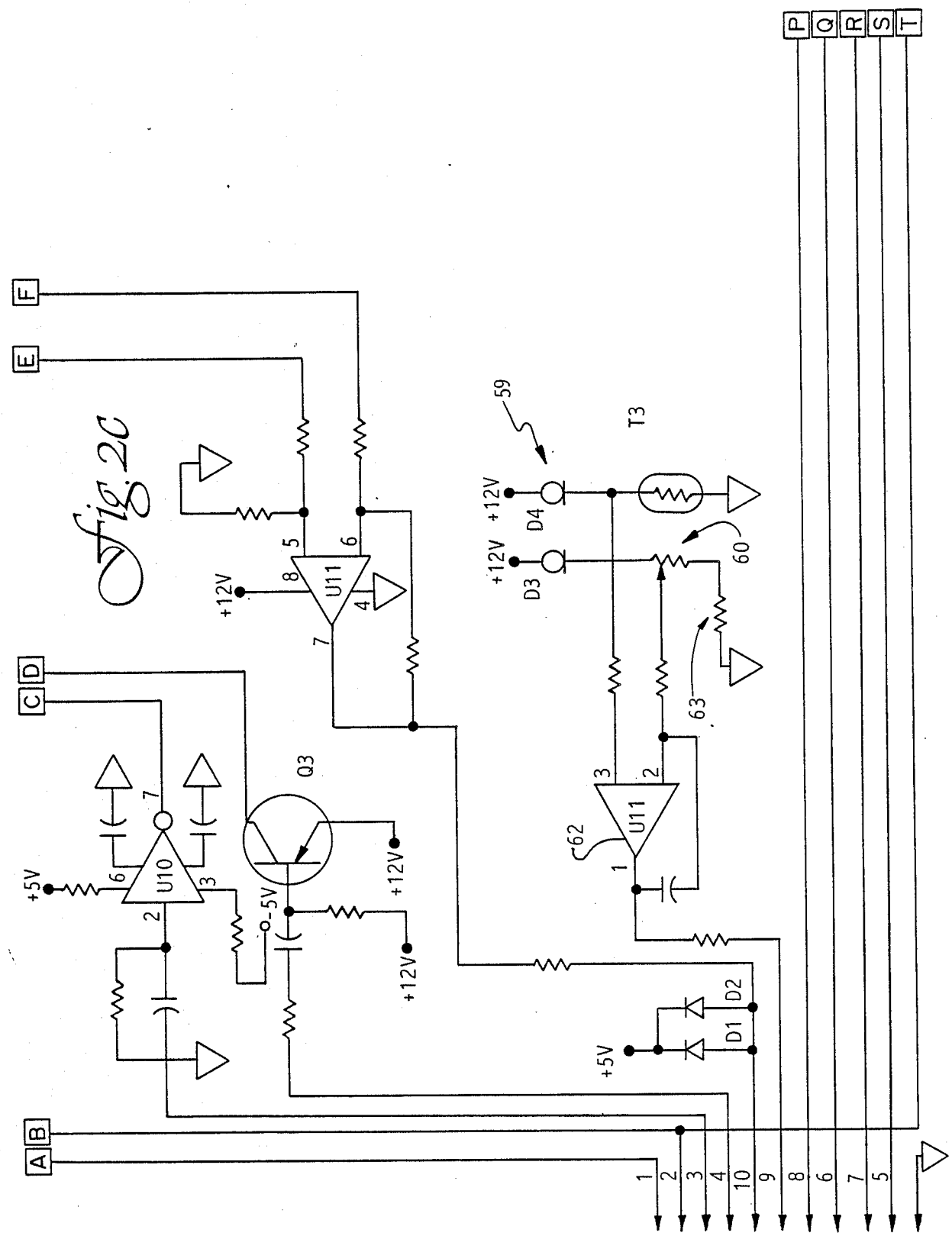

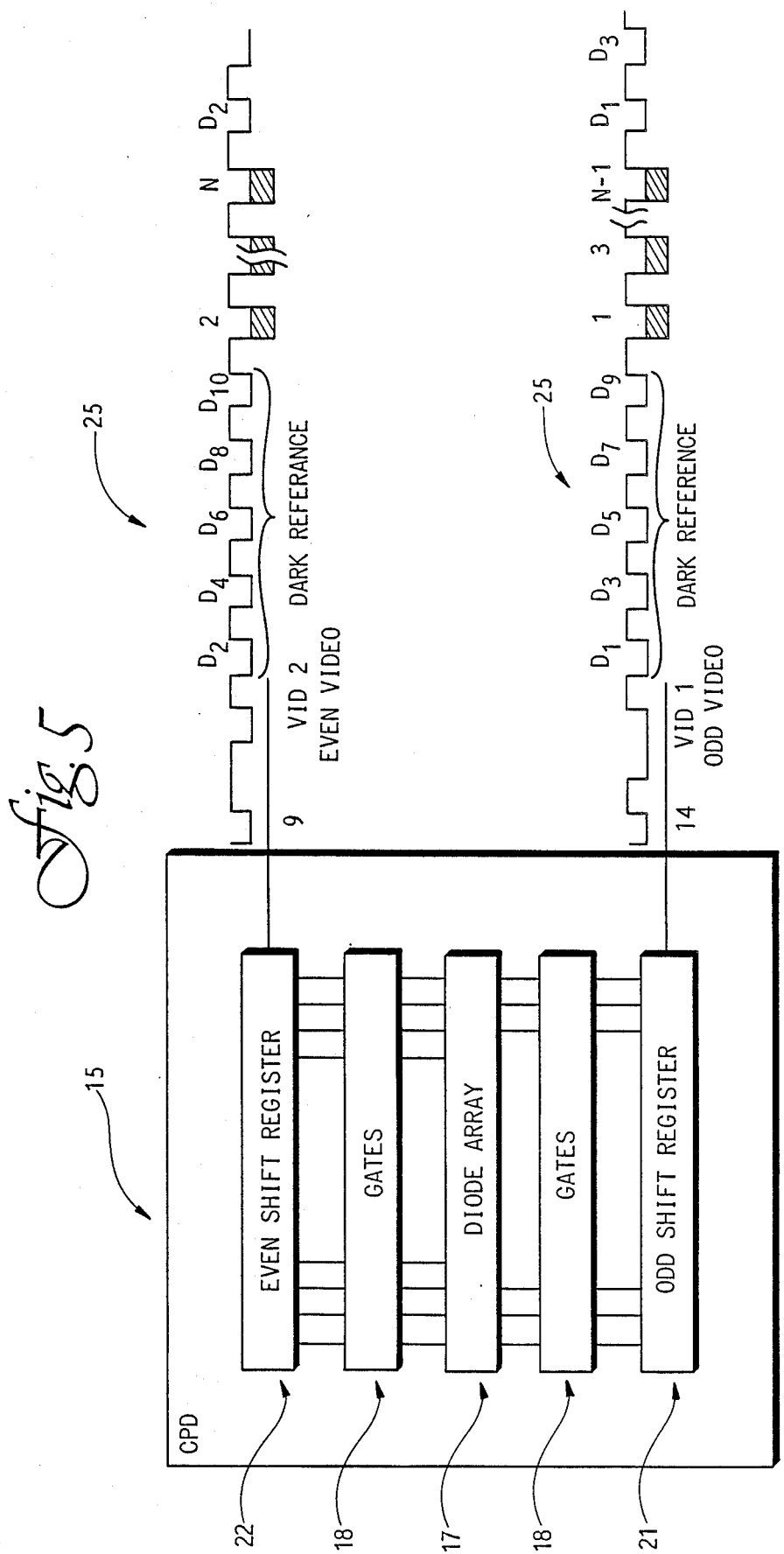

DARK SIGNAL COMPENSATION FOR DIODE ARRAYS

BACKGROUND OF THE INVENTION

The field of the invention is scanning densitometers, measuring instruments which determine the density distribution of a graphic image. More particularly the invention relates to cooling means and correction circuits which enhance the accuracy of density measurements by minimizing the detrimental effect of thermal noise generated in a diode array which is used to make the density measurements.

Density measurements, the determination of highlight, midtone and shadow denisties on a graphic image, have in the past been a subjective evaluation and determination which is very time consuming. The operator generally used a hand-held densitometer and subjectively chose the brightest, the darkest and other areas of a graphic image for measurement and for entry into a reproduction system. There has been a clear and long felt need for automation of this process.

Density measurements, however, are logarithmic. Consequently on a ten volt measurement scale the following relationships may exist: 10 volts equal 0 density; 1 volt equals 1.0 density; 0.1 volt equals a 2.0 density; 0.01 volt equals a 3.0 density; and 0.001 volts equals a 4.0 density. Therefore, distinguishing densities between 3.5 and 3.6 with available automated technology requires extreme accuracy in measurement and is extremely difficult to achieve.

The measurement is complicated when using charge coupled diode arrays by a phenomena referred to as "dark signal". When the cells of a photodiode array are exposed to light they charge in proportion to the amount of light falling on the cell. During the exposure time the charge is accumulated to a specific charge which is then transferred by gates to a shift register, out of which the data is read for conversion and processing. The accuracy of the measurement is effected by electron noise or thermal noise generated in the cell sites and in the shift register. In a commercially available photodiode array with a 30 millesecond integration time and at 20° centigrade, dark signal and dark signal nonuniformity are proportional to the integration time and approximately doubles for every 7° centigrade increase in temperature. This presents a complimentary problem because not only do the cells accumulate dark signal or thermal noise, they also accumulate it non-uniformly. To obtain accurate measurements, therefore, it is necessary to control the amount of dark signal generated and to compensate to the extent possible for any dark signal or thermal noise which is generated.

SUMMARY OF THE INVENTION

Three means or methods are provided to address the problem of dark signal and to thereby enhance the accuracy of readings derived from a photodiode array. The photodiode array is located in an insulated camera housing to receive light focused on it through a lens, the light intensity signifying the density of the image being scanned or measured. A first means or method of minimizing thermal noise is provided by maintaining the internal temperature of the camera and therefore the temperature of the diode array as close to ten degrees centigrade as possible. This is achieved with a refrigeration unit including a heat exchanger which cools the diode array as necessary depending on variations of the internal temperature surrounding the photodiode array.

To further compensate for the slight swings in temperature due to cooling and lack of cooling within the variation around ten degrees centigrade that the refrigeration unit provides, a temperature compensation circuit driven by a thermistor is provided varying the reading upwardly or downwardly depending upon the minimal temperature drift detected by the thermistor.

To minimize any effect of electron noise inherently generated by the photodiode array in spite of the controls provided and described above a calibration means or method is also provided which can take one of two alternative forms. A paddle can be rotated over the diode array and data read from each cell for individual calibration of each cell. This dark reference data can then be subtracted from the cell readings to minimize or eliminate any residual or inherent noise created in the cell sites or shift register. Alternatively dark current readings from leading cells, which are masked by an oxide mask in the photodiode array, can be received and used to correct for inherent electron noise. This data is stored and subtracted from the reading by a microprocessor during the processing of the data.

It is an object of the invention to enhance the accuracy of data read from a charge coupled diode array.

It is an object of the invention to minimize the effect of thermal noise on readings obtained from a charge coupled linear photodiode array.

It is an object of the invention to maintain the temperature of a diode array at or about ten degrees centigrade to minimize the effect of thermal noise.

It is an object of the invention to electronically compensate for temperature variations of a photodiode array to enhance the accuracy of readings therefrom.

It is an object of the invention to provide a calibration of the readings from a photodiode array to minimize the effect of electron noise on readings obtained therefrom.

It is an object of the invention to enhance the accuracy of readings from a charge coupled linear photodiode array by an order of magnitude.

DESCRIPTION OF THE DRAWINGS

FIG. 1 shows the connection of the cooling system to the camera. FIG. 1a is a side elevational view showing the refrigeration unit, the heat exchanger and how it is connected to the camera. FIG. 1b is a rear elevational view with the back of the camera housing removed. FIG. 1c is a schematic of the cooling system showing the solenoid valves used to supply cold liquid to the heat exchanger and to bypass the heat exchanger under control of the temperature sensing devices.

FIGS. 2, 2a, 2b, 2c and 2d describe a schematic diagram of the temperature compensating circuit.

FIG. 5 shows the charge-coupled linear photodiode array. The array is shown in block diagram form with output signals identifying the dark reference readings.

DESCRIPTION OF THE PREFERRED EMBODIMENT

Figure 2A:
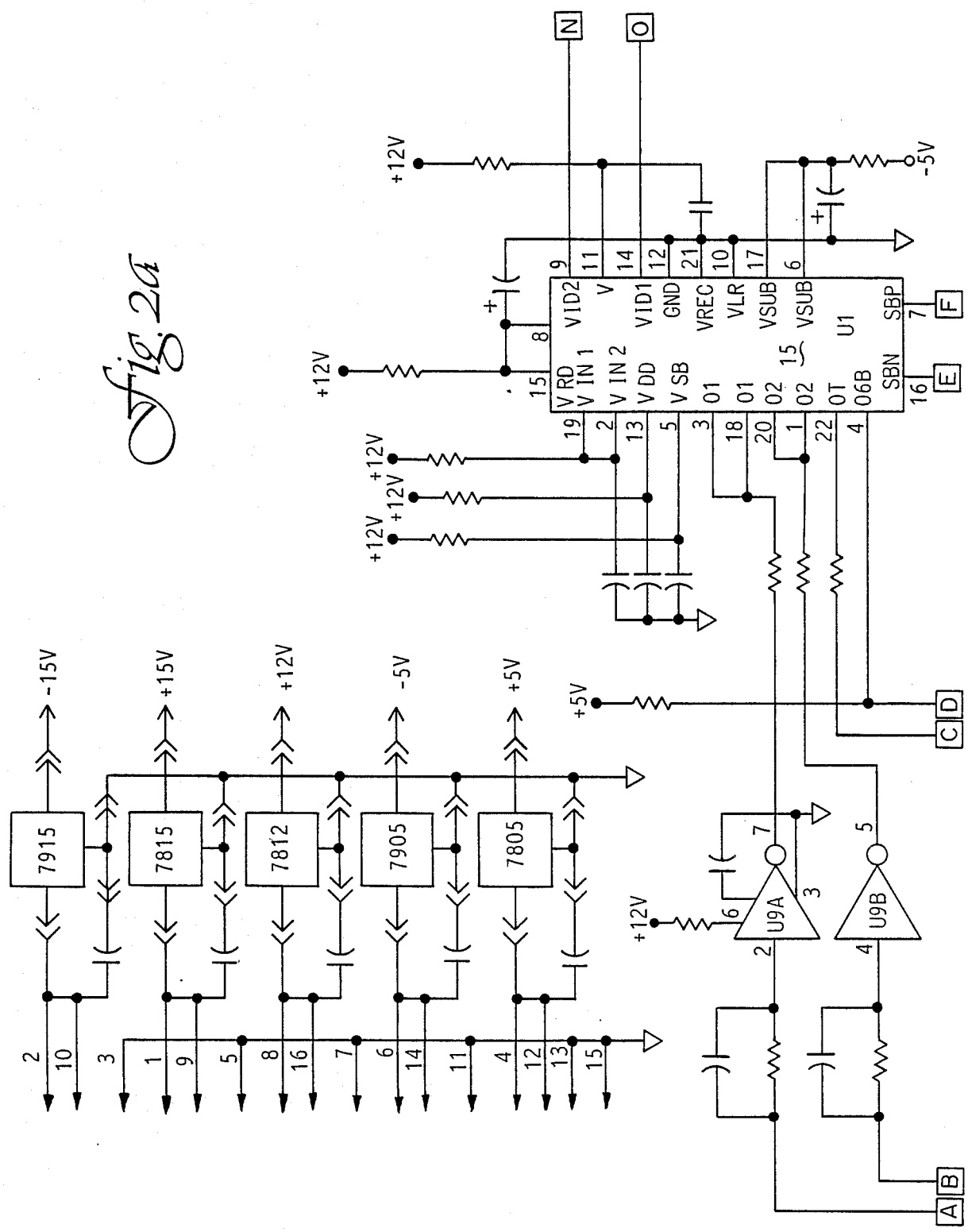

The invention is designed to measure the densities of a graphic image which is projected through a lens 12 onto a charge-coupled linear photodiode array (CPD) 15 such as those manufactured by Reticon Corporation under Manufacturer's designation RL0512D for an array having 512 elements. Such arrays are available with 256 elements, 1024 elements or 2048 elements as well with the numeric portion of the manufacturer's designation modified accordingly.

The design of CPD's, 15 as well as other charge-coupled devices, includes the cell sites 17 which charge proportionally upon exposure to an intensity of light falling on the diode (or capacitor), gates 18 which switch the charge into a shift register 21 or 22 for read-out and normally odd and even shift registers 21,22 out of which are clocked the readings 25 for processing. It is a fundamental characteristic of such devices 15 that for every five to ten degrees centigrade of temperature increase the amount of dark signal, or dark current doubles. This electron or thermal noise, referred to as dark signal or dark current, is proportional to the temperature of the diode array 15.

With no response (shadow) the output of the diode array is approximately six volts. With full exposure to light (highlight) the output is about five volts. This range is preferably inverted and referenced to ground over a ten volt range. Since density measurement and response is logarithmic, a ten volt range of data requires measurement and processing of 10 volts, $10°$ volts, $10^{-1}$ volts, $10^{-2}$ volts, $10^{-3}$ volts, and even $10^{-4}$ volts. These measurements relate to zero to four density. Therefore, thermal drift of a small amount has a drastic effect on the accurate measurement of shadow density. The potential for thermal noise exists in the diode array, during charge time, and in the shift register while values are being clocked.

According to the present invention, three means or methods are provided to stablize the readings from the photo sites, refrigeration, temperature compensation and calibration. Using a refrigeration unit 30 the temperature of the diode array 15 is maintained as close to ten degrees centigrade as possible. This stabilizes the photo sites 17 and makes them as effective as possible. Additional temperature compensation is provided for the minor temperature shifts around ten degrees centigrade to correct for dark current or thermal noise generated in the photo sites 17 and the shift registers 21,22. Finally, no light readings for all photo sites 17, or alternatively leading photo sites which are masked, can be read and stored for calibration purposes. Thus, any remaining accumulation of thermal noise after refrigeration and compensation can be subtracted from the actual readings to generate data accuracy approaching 4.0 density. The advantage of calibrating all photo sites 17 addresses non-uniformity of individual photo sites 17. However, with control of temperature and temperature compensation the use of the masked photo sites 17 yields a real-time same-scan calibration which reflects the actual temperature variations during the reading time and, because of the temperature compensation, provides adequate calibration for residual thermal noise or dark current.

Referring to FIG. 1, the refrigeration control is shown and can be understood. A liquid chiller 35, commercially referred to as Endocal is utilized. The cooled glycol is pumped into a heat exchanger 37 having a radiator or condensor. The heat exchanger 37 also includes a fan system to circulate cooled air through the camera 40. Between the inlet and the return lines 42,44 a bypass line 46 is used with a thermistor T3 controlled solenoid valve 52 which is opened when the desired internal camera temperature is achieved as measured by the thermistor T3. When the temperature increases, a second solenoid valve 54 is opened to maintain flow to the heat exchanger 37.

The cold air from the heat exchanger 37 is blown through an inlet duct 56 into the camera housing 41. A return air duct 58 is also provided to return air to the heat exchanger 37 for cooling. The camera housing 41 is insulated with a foam core insulation 59 to maintain the internal temperature of the camera 40 and the CPD array 15 as constant as possible.

Little thermal noise exists at ten degrees centigrade. The refrigeration unit 30 maintains the CPD array 15 at a temperature of ten degrees centigrade plus or minus one half degree as the solenoid valves 52,54 control the cooling of the CPD 15 array under control of the temperature sensing thermistor T3 which forms part of the temperature control circuit.

Figure 2B:
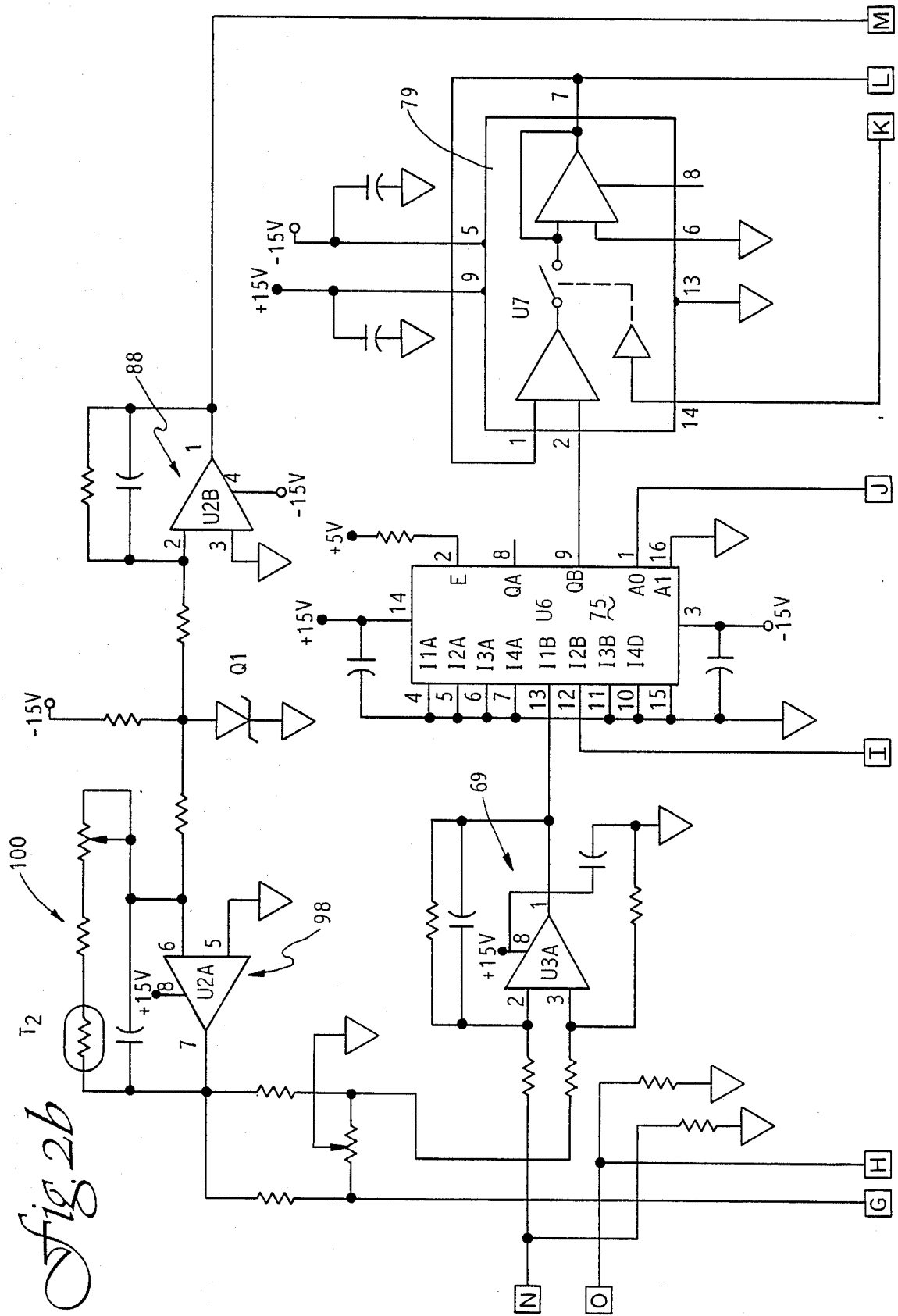
Figure 2D:
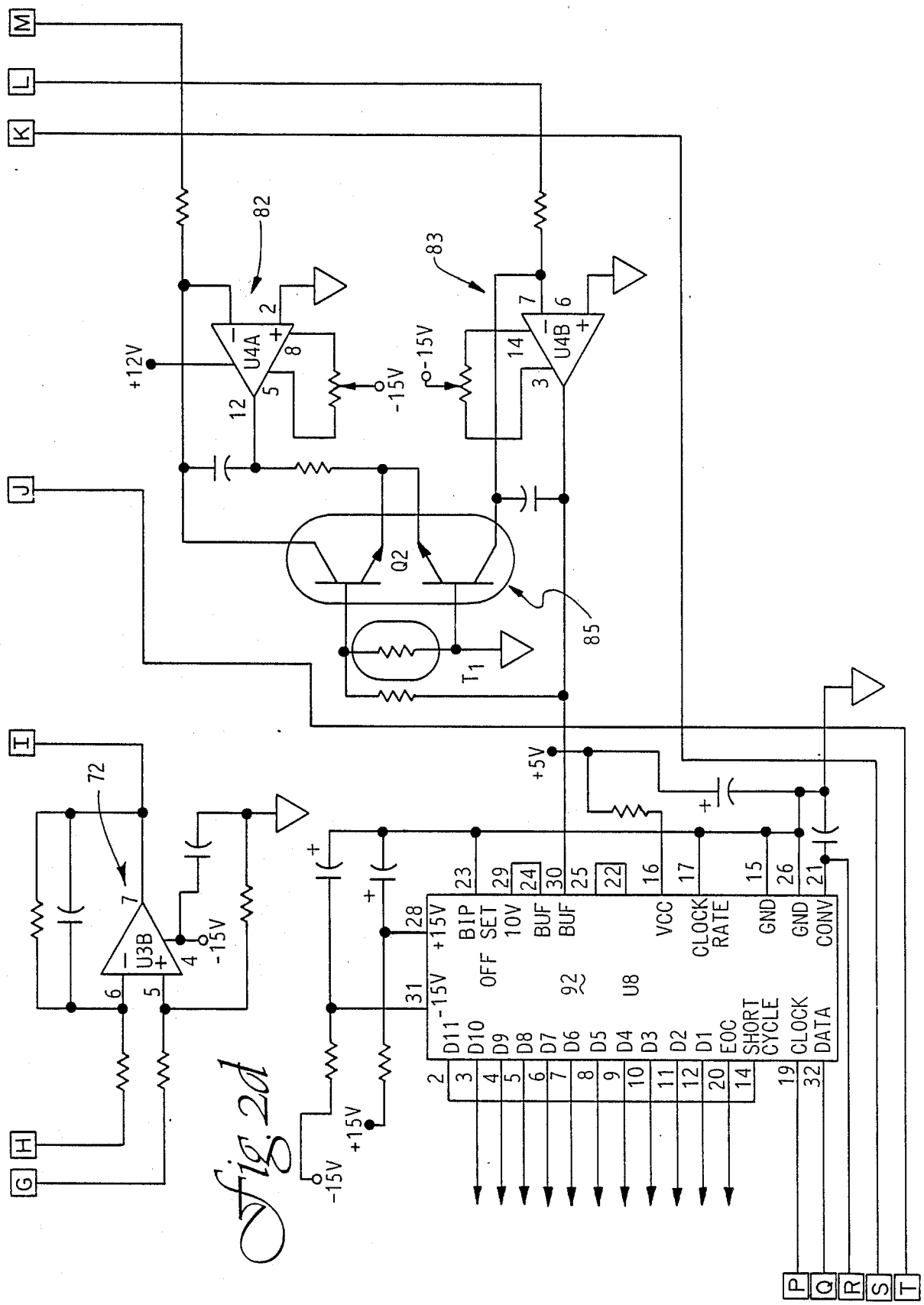
Figure 3:
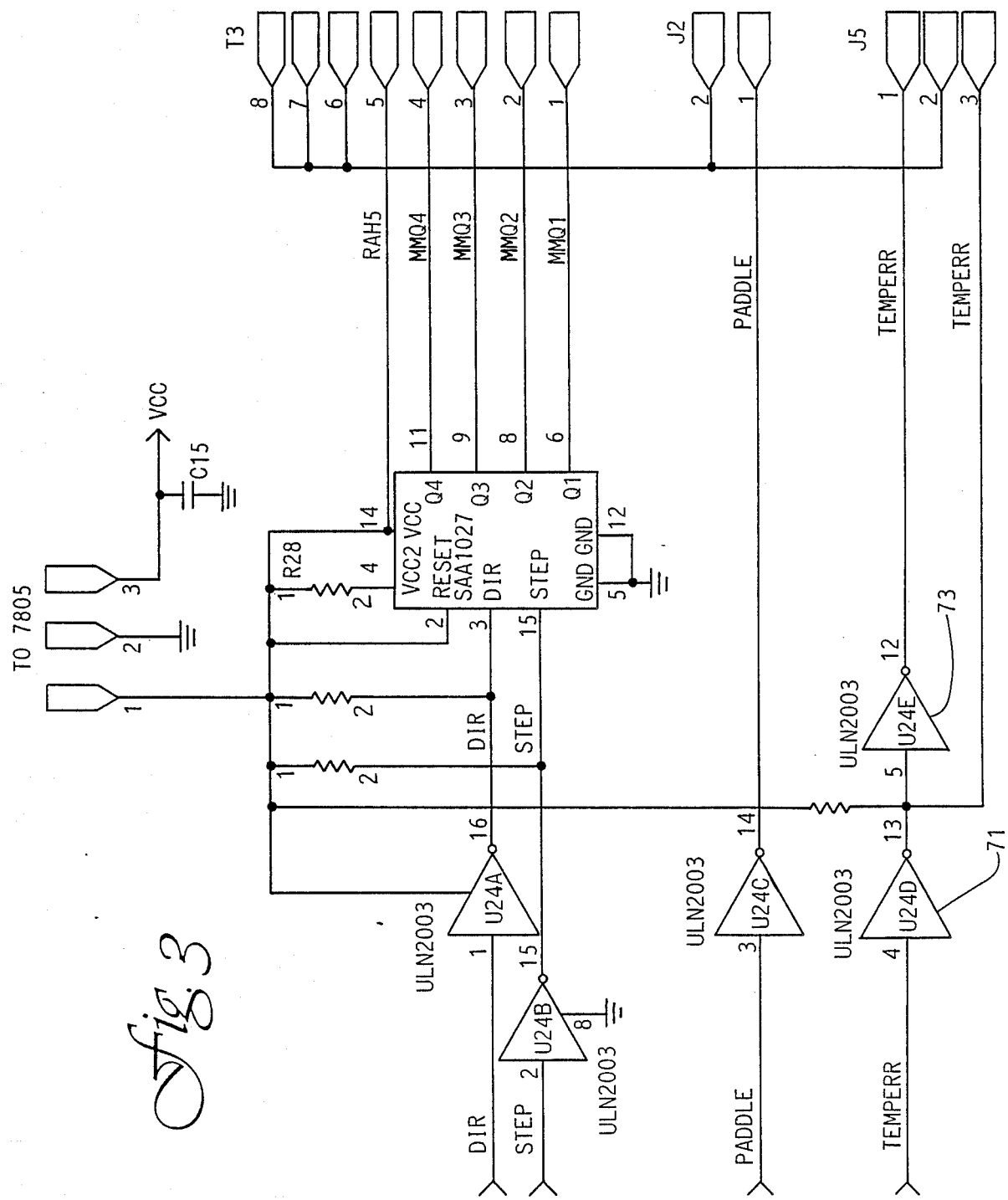
FIGS. 3 and 4 show control components.
Figure 4:
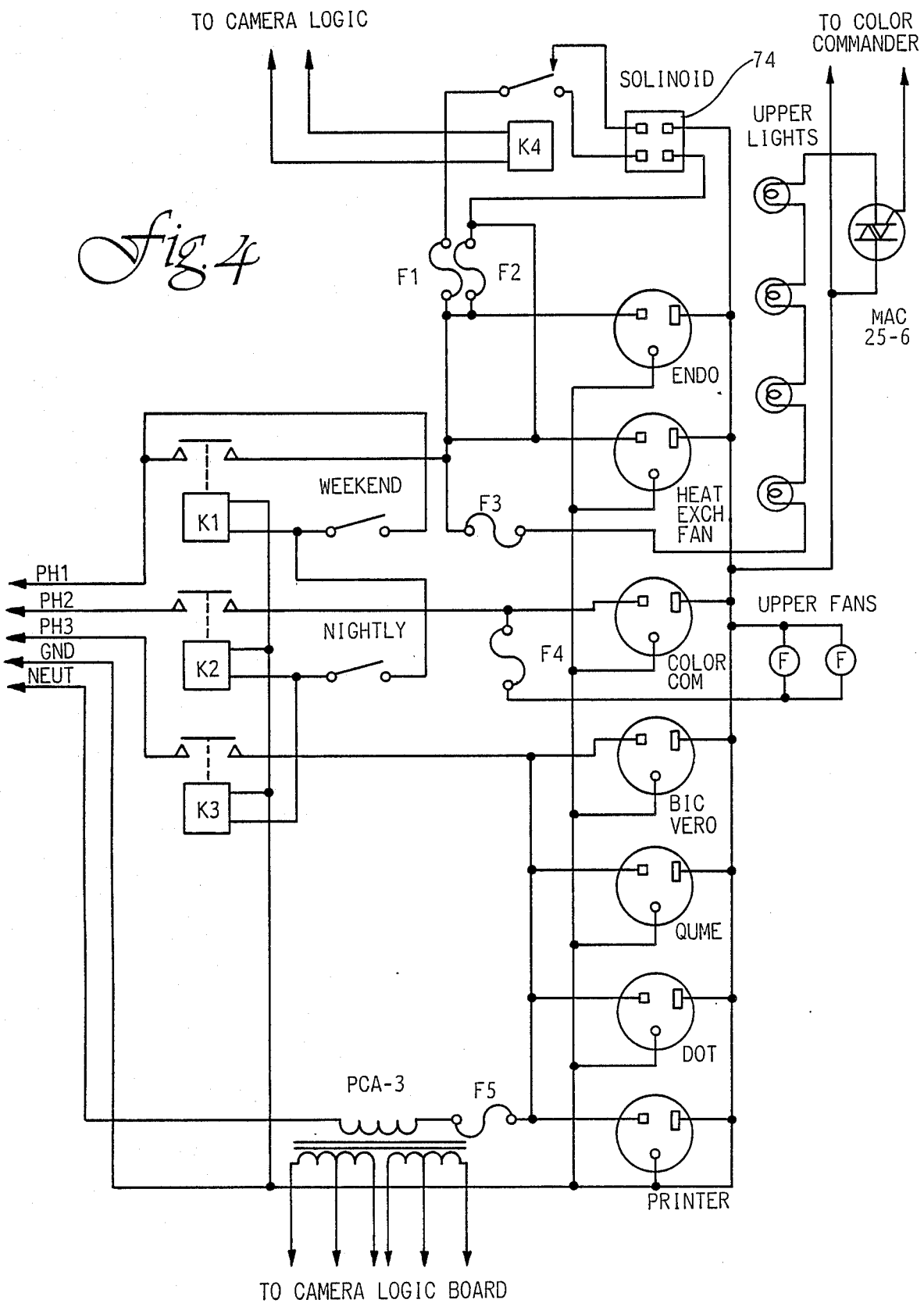

Referring now to FIGS. 2 through 4, control of the solenoid valves 52,54 and temperature compensation are shown and can be understood. The CPD array 15, is positioned and travels behind the lens 12 of the camera 40. A small bead thermistor T3, with a very fast temperature response is physically located immediately adjacent the CPD array 15. A constant current source D4, manufacturer's designation CRO 33, is connected through the nominal 1000 ohm thermistor T3 the resistance of which is temperature dependent. The output of the thermister T3 is connected to a comparator 62. On the second input of the comparator 62 is a second constant current generator D3 with a thousand ohm trimmer resistance 60 and a 733 ohm bias resistor 63 which gives a sufficient operating temperature with the ability of adjustment. As the temperature of the thermistor T3 varies, and its resistance, the output of the buffer 62 goes high or low which is used to control the refrigeration solenoid valves 52,54. This generates the signal designated "temperature error".

As shown on FIG. 3, the temperature error signal is double buffered by buffers 71 and 73. This provides temperature error signal of both polarities using contacts 1 and 2 or 2 and 3 so that a variety of solenoids, may be used with the invention.

Shown in FIG. 4 are the connections to the solenoid relay K4, which is a double acting solenoid 74 which opens the bypass valve 52 and closes the heat exchanger solenoid valve 54 if the temperature is swinging below ten degrees centigrade and, conversely, opens the heat exchanger valve 54 and closes the bypass valve 52 if the temperature is increasing above ten degrees centigrade. The thousand ohm trimming resistor 60 is accessible from the back of the camera housing 41 through a self-insulating plastic cap which can be removed to adjust the temperature sensitivity.

As also shown in FIG. 5, the outputs from the photo-diode array 15 are designated VID 1 on pin 14 and VID 2 on pin 9, the VID 1 signal being odd bits from one shift register 21, and VID 2 being even bits from the other shift register 22. These outputs are connected to two buffer circuits 69 and 72 where they are inverted and referenced to ground. The outputs vary from zero to 10 volts where no light is represented by the zero volt signal and maximum light (saturation exposure) is 10 volts. The outputs are connected to a multiplexer 75 to consolidate the odd and even readings into a single train of data.

The output of the multiplexer 75 on QB, pin 9, is connected to a sample and hold circuit 79 to convert the data readings to voltage levels.

Two operational amplifiers 82,83 and a dual NPN transistor 85, with an associated thermistor T1, is used for a logarithmic conversion circuit. A reference voltage generated by an operational amplifier 88 is connected to one of the operational amplifiers 82. The output of the sample and hold circuit 79 is connected to the other operational amplifier 83. The logarithmic relationship between the base current and emitter base voltage of the dual NPN transistor 85 is used for the logrithmic conversion. Thermistor T1 keeps transistor 85 operating at the same bias level to give the circuit stability.

The logarithmic output of transistor 85 is connected to an analog to digital converter 92, the output of which is connected to a microprocessor (not shown) for processing.

While thermistor T3, the associated solenoid valves 52,54 and refrigeration system 30 keep the environment of the CPD 15 as stable as possible there is still an approximate plus or minus one-half degree centigrade of temperature variation as the cooling process cycles under control of the temperature control circuit 58. Additional temperature compensation within that small deviation is provided by a temperature compensation circuit 100, including a third thermistor T2, which with operational amplifier 98 is connected to the positive inputs of operational amplifiers 71 and 72 to put out a voltage which is reversely proportional to the small temperature deviation determined by the thermistor T2 not compensated for by the refrigeration. The output of the temperature compensation circuit 100 is on the order of 0.0075 volts per degree centigrade in correction which is sufficient to compensate for the plus or minus one-half degree swing of the internal temperature of the camera housing 41.

Referring now to FIGS. 1 and 3, two alternative methods are provided for calibration of the CPD array 15. As shown in FIG. 1, a rotary solenoid actuated paddle or filter 110 can be rotated over the CPD array 15 for calibration purposes. A set of readings 25 can then be taken, which are temperature controlled and temperature compensated, as calibration data for the CPD array 15. If the residual thermal noise of every photo site, including the dwell time in the site and the shift register 21 or 22 is measured, this set of data can be stored in microprocessor memory and this last vestige of electron or thermal noise subtracted from measured data readings. Every site calibration addresses the non-uniformity of the various cell sites and their receptivity to thermal noise or dark current.

Alternatively, as shown in FIG. 5 the leading photo sites D1-D10 of the CPD array 15 are masked with an oxide mask. The readings 25 from these sites, therefore, represent the final vestige of thermal noise that may be generated during the actual operation during the read cycle. Since the CPD array 15 is used on a constant duty cycle, on and off time has no effect. And, since the thermal noise has been substantially eliminated by the controlled and compensated temperature, the dark current measurements from the mask sites is sufficiently accurate for calibration purposes to obtain real time data values to subtract from the density readings.

It will be clear to those skilled in the art that each of the three means or methods of controlling or compensating for dark signal will enhance the operation and accuracy of the density readings which are the object of the invention. In the present invention, however, the three means or methods are cascaded together to produce very stable readings which increase the accuracy of the readings by an order of magnitude. It should be understood that various modifications and variations of the means and methods described may be resorted to without departing from the spirit of the invention as those skilled in the art will readily understand. Such modifications and variations are considered to be within the purview and scope of the present invention as defined by the following claims.

Having described my invention I claim:

1. Apparatus for measuring the densities of a graphic image comprising:
   means for exposing a monolithic diode array having a plurality of cell sites to light intensity representing the density of the graphic image;
   output means operably coupled to said monolithic diode array for providing an electrical output representative of said light intensity;
   logarithmic converting means operably coupled to said output means for converting said electrical output to a logarithmic representation of said light intensity; and
   means for minimizing the effect of thermal noise generated in the monolithic diode array operably coupled to said output means and said logarithmic converting means, whereby said logarithmic representation of said light intensity provides a consistently accurate representation of the density of said graphic image.

2. The apparatus as claimed in claim 1, said logarithmic converting means including means for providing a reference signal and comparison means for comparing said electrical output to said reference signal.

3. The apparatus as claimed in claim 2, said comparison means comprising semiconductor means, said means for minimizing the effect of thermal noise including biasing temperature compensation means operably coupled to said semiconductor means for providing said semiconductor means with a stable biasing level.

4. The apparatus as claimed in claim 1, said means for minimizing the effect of thermal noise including electrical output temperature compensating means operably coupled to said output means, said electrical output temperature compensating means providing an adjusting signal for adjusting said electrical output in relationship to the temperature of said monolithic diode array, whereby said logarithmic converting means is provided with a temperature compensated electrical output representation of said light intensity.

5. The apparatus as claimed in claim 4, said monolithic diode array including a plurality of video output signals representative of said light intensity, said output means including multiplexer means for combining said video output signals and said adjusting signal into said electrical output representative of said light intensities.

6. The apparatus as claimed in claim 5, said logarithmic converting means including means for providing a reference signal and comparison means for comparing said electrical output to said reference signal.

7. The apparatus as claimed in claim 6, said comparison means comprising semiconductor means, said means for minimizing the effect of thermal noise including biasing temperature compensation means operably coupled to said semiconductor means for providing said semiconductor means with a stable biasing level.

8. The apparatus of claim 1 wherein the means for minimizing the effect of thermal noise comprises refrigeration means for maintaining the temperature of the diode array at an operating temperature of about ten degrees centigrade and electrical output temperature compensating means operably coupled to said output means for providing an adjusting signal for adjusting said electrical output in response to differences of the actual temperature of the diode arrays relative to said operating temperature whereby said logarithmic converting means is provided with a temperature compensated electrical output representation of said light intensity.

9. The apparatus as claimed in claim 8, said monolithic diode array including a plurality of video output signals representative of said light intensity, said output means including multiplexer means for combining said video output signals and said adjusting signal into said electrical output representative of said light intensities.

10. The apparatus as claimed in claim 9, said logarithmic converting means including means for providing a reference signal and comparison means for comparing said electrical output to said reference signal.

11. The apparatus as claimed in claim 10, said comparison means comprising semiconductor means, said means for minimizing the effect of thermal noise including biasing temperature compensation means operably coupled to said semiconductor means for providing said semiconductor means with a stable biasing level.

12. The apparatus of claim 1 wherein the means for minimizing the effect of thermal noise comprises means for calibrating the cell sites by measuring the thermal noise signals generated within said cell sites with no light exposure to provide a set of calibration values and subtracting said calibration values from the signals generated within said cell sites when the monolithic photodiode array is exposed to light.

13. The apparatus as claimed in claim 12, said means for calibrating the cell sites including means for selectively covering said diode array to prevent light from impinging on said array.

14. The apparatus as claimed in claim 12, said means for calibrating the cell sites including means for permanently covering selected cell sites of said diode array to prevent light from impinging on said selected cell sites, and means for estimating the thermal noise generated in the remaining of said cell sites from the actually measured thermal noise in said selected cell sites.

* * * * *

UNITED STATES PATENT AND TRADEMARK OFFICE
CERTIFICATE OF CORRECTION

PATENT NO. : 4,933,543

DATED : June 12, 1990

INVENTOR(S) : Frank A. Hull

It is certified that error appears in the above-identified patent and that said Letters Patent is hereby corrected as shown below:

Column 4, line 14, insert the number "59" after the word "circuit".

Signed and Sealed this

Twenty-sixth Day of November, 1991

Attest:

HARRY F. MANBECK, JR.

*Attesting Officer*      *Commissioner of Patents and Trademarks*